(12) United States Patent
Wang

(10) Patent No.: US 6,665,429 B1
(45) Date of Patent: Dec. 16, 2003

(54) METHOD AND APPARATUS FOR MICROBIOLOGICAL DISK RECOGNITION

(75) Inventor: Qi Wang, Santa Barbara, CA (US)

(73) Assignee: Giles Scientific, Inc., Santa Barbara, CA (US)

( * ) Notice: Subject to any disclaimer, the term of this patent is extended or adjusted under 35 U.S.C. 154(b) by 620 days.

(21) Appl. No.: 09/668,525

(22) Filed: Sep. 22, 2000

(51) Int. Cl.[7] .................................................. G06K 9/00
(52) U.S. Cl. ...................... 382/128; 435/32; 435/173.8; 435/176; 435/177; 435/182
(58) Field of Search ................................ 382/128, 129, 382/130, 131, 132, 133, 134; 435/9, 29, 32, 173.8, 174, 176, 177, 182, 202, 287.3, 287.5, 390; 377/10; 600/473

(56) References Cited

U.S. PATENT DOCUMENTS

| | | | |
|---|---|---|---|
| 3,757,299 A | 9/1973 | Perry | 382/128 |
| 3,811,036 A | 5/1974 | Perry | 377/10 |
| 4,203,029 A | 5/1980 | Kitchener et al. | 377/10 |
| 4,355,228 A | 10/1982 | Sama et al. | 348/251 |
| 4,448,534 A * | 5/1984 | Wertz et al. | 356/435 |
| 4,701,850 A | 10/1987 | Gibbs | 435/32 |
| 4,724,215 A * | 2/1988 | Farber et al. | 435/287.3 |
| 4,959,552 A * | 9/1990 | Saffert et al. | 250/559.26 |
| 5,290,701 A * | 3/1994 | Wilkins | 435/287.3 |
| 5,817,475 A | 10/1998 | Gibbs et al. | 435/29 |
| 6,107,054 A * | 8/2000 | Gibbs | 435/32 |
| 6,153,400 A * | 11/2000 | Matsumura et al. | 435/32 |

FOREIGN PATENT DOCUMENTS

WO  WO 00/11593  3/2000

OTHER PUBLICATIONS

An Introduction to Automatic Image Analysis. Morton, Roger, Bausch & Lomb, May, 1984, pp. 1–20.
From Image to Analysis: Object detection and measurement. Bender, Michael K. *American Laboratory*, Feb., 1984.

* cited by examiner

Primary Examiner—Jayanti K. Patel
Assistant Examiner—Abolfazl Tabatabai
(74) Attorney, Agent, or Firm—R. Neil Sudol; Henry Coleman; William Sapone (57) ABSTRACT

A method and associated apparatus for use in a microbiological assay procedure wherein a plurality of diffusion disks are placed on a nutrient medium on a plate, each of the disks carrying a respective antibiotic agent and each having an identification code identifying the respective antibiotic agent, the disks being positioned on the plate in a preselected relative arrangement. The method comprises optically scanning the disks on the plate, consequently generating a digitally encoded image including digitized representations of the identification codes, and electronically processing the digitally encoded image to determine an angle of rotation of the plate relative to a pre-established reference frame or coordinate system, wherein the electronic processing of the digitally encoded image includes detecting a region of the plate occupied by a unique subset of the disks. The digitally encoded image is processed to determine, for at least one of the identification codes on the disks, a numerical value of at least one overall pattern parameter. The determined numerical value of the pattern parameter is electronically compared with electronically stored premeasured values of the pattern parameter for the identification codes on the disks, to automatically identify at least one disk from among the disks on the plate.

60 Claims, 3 Drawing Sheets

METHOD AND APPARATUS FOR MICROBIOLOGICAL DISK RECOGNITION

BACKGROUND OF THE INVENTION

This invention relates to a method and an associated apparatus for automatically determining positions of antibiotic-containing disks in a microbiological testing procedure.

Agar disk diffusion is a widely recognized microbiological assay for measuring susceptibility—a parameter effectively defined by the assay itself. The susceptibility of a microorganism to a given antibiotic is essentially a description of the size of the inhibitory zone resulting from placement of a permeable disk impregnated with the given antibiotic onto an agar surface inoculated with a sample culture of the microorganism. This parameter provides a measure of the ability of the antibiotic compound to stem growth of the target culture, but it is also a complex function of diffusion constants and other kinetic factors.

Of additional use to the clinician is a related quantitative measure of susceptibility, known as "minimum inhibitory concentration"(MIC). Although still requiring additional information to translate the parameter into a prescription for clinical practice, this quantitative measure eliminates some sources of complexity and uncertainty relative to qualitative susceptibility. A additional useful clinical parameter is the "inhibitory quotient", which expresses the ratio of the drug concentration in a particular body tissue at a lowest clinical dose to the minimum inhibitory concentration.

The MIC is ideally determined by an assay appropriately called the dilution method, which straightforwardly involves inoculating a series of test tubes with the target culture, the test tubes containing a series of dilutions of the target antibiotic. One series of test tubes therefore tests only one culture and one antibiotic, in contradistinction to an agar diffusion assay petri dish, which may test a plurality of antibiotics simultaneously with less material and expense. The advantage of the dilution method is that it provides less ambiguously interpretable quantitative results relative to the agar diffusion method, while its disadvantage is primarily its expense, both in materials and labor.

It is therefore desirable to have a device which automatically translates a dimension of an inhibition zone on an agar diffusion assay plate into a more clinically useful quantitative measure of drug-bacterium interaction, such as the MIC. Such a device is disclosed by U.S. Pat. No. 4,701,850. It is further desirable to have a device which automates the process of reading the apposite linear dimension of the inhibition zone, such devices being revealed in subsequent United States patents. The relation of the diameter of the inhibition zone to the MIC for an unknown biological agent is approximated by a linear relation, the parameters for which assumed relation for a particular antibiotic being determined by statistical estimation based on the scatter of data points whose coordinates are inhibition zone diameters and actual minimum inhibitory concentrations determined by dilution assay for a particular microorganism, the relation being assumed linear and being assumed to persist for untested organisms.

Current commercial microbiological assay machines have largely automated the detection or measurement of agar-plate drug diffusion zones. One current automated test plate reader system requires the user to determine and record the positions of all drug disks on agar plates or panels. While inserting a test plate in the reader, the user must align a reference disk as prompted on screen with a mark on the reader drawer (reference disk is user-defined during drug panel setup). The software then searches for all disks and assigns a correct drug name to each disk based on identified orientation of the reference disk. Each plate is searched for disks in an area approximately 24 mm around the usually 6 mm diameter disk position assigned during drug panel setup. Because the drug code printed on all disks is small and difficult to read visually, it would be a significant advantage for the system to determine a reference disk position automatically without having users align it specifically to the drawer mark.

Sometimes a drug disk may be dropped on the plate in the wrong position(s), or the user may have selected the wrong drug panel name containing the wrong drug disk names. It would be another significant advantage for the system to detect if drug disk(s) were misplaced; this would improve the quality control and reliability of the result reading.

One known technology which has been proposed for use in automatic identification of microbiological assay disks is optical character recognition (OCR) technology. This technology requires input of the orientation of the target characters on each disk prior to reading and recognizing them. It is inherently difficult to know character orientation without an orientation mark in addition to the drug code on each disk. Conventional OCR technology is difficult without an orientation mark, but it can be done through extensive computer processing to assess multiple possible orientations of each disk. Providing an orientation mark on each disk is a solution limited in its usefulness insofar as it requires the supply of special disks in substitution for conventional commercially available disks.

OBJECTS OF THE INVENTION

An object of the present invention is to provide an improved apparatus and/or associated method for use in microbiological testing.

A more specific object of the present invention is to provide a microbiological testing apparatus and/or method wherein positions of antibiotic-containing disks are automatically determined.

A related object of the present invention is to provide a microbiological testing apparatus and/or method wherein the zone surrounding a given antibiotic disk is associated with the subject antibiotic compound without further operator intervention or opportunity for human error.

Yet another related object of the present invention is to provide a microbiological testing apparatus and/or method which does not require orientation marks on the disks and the extensive computer processing required by conventional OCR to read codes without that mark.

It is a supplemental object of the present invention to provide such a microbiological testing apparatus and/or method which is inexpensive to use.

A further object of the present invention is to provide an essentially automated microbiological testing apparatus and/or method wherein a dimension of an inhibition zone associated with an antibiotic impregnated disk on an agar plate is measured automatically.

A more particular object of the present invention is to provide such a microbiological testing apparatus and/or method which facilitates association of a microorganism susceptibility measurement with a particular antibiotic agent.

These and other objects of the present invention will be apparent from the descriptions and illustrations provided herein.

SUMMARY OF THE INVENTION

A method in accordance with the present invention is adapted for use in a microbiological assay procedure wherein a plurality of diffusion disks are placed on a nutrient medium on a plate, each of the disks carrying a respective antibiotic agent and each having an identification code identifying the respective antibiotic agent, the disks being positioned on the plate in a preselected relative arrangement. The method comprises optically scanning the disks on the plate, consequently generating a digitally encoded image including digitized representations of the identification codes, and electronically processing the digitally encoded image to determine an angle of rotation of the plate relative to a pre-established reference frame (coordinate system), wherein the electronic processing of the digitally encoded image includes detecting a region of the plate occupied by a unique subset of the disks.

The unique subset of the disks may include an absence of a disk in a location within the region, or a pattern or configuration of disks in the region. The unique subset of the disks may alternatively include a reference disk having a unique characteristic relative to other disks on the plate. The unique characteristic may be the area of the respective identification code on the reference disk, an ordered pair of ratio of length and width of the respective identification code, or an ordered pair or ratio of light and dark pixels within the respective identification code. Generally, it is contemplated that the length and width parameters, as well and the light and dark pixels, are measured or counted after the establishing of an outline for the respective identification code.

Where the unique reference characteristic is area, the electronic processing of the digitally encoded image includes (1) digitally processing the digitally encoded image to determine estimates of areas occupied by the identification codes on the disks, and (2) electronically comparing the determined area estimates with prestored identification code areas to automatically distinguish the identification code of the reference disk from among the identification codes of the other disks on the plate.

Where the unique reference characteristic is the length and width combination (e.g., ratio) of a drug carrying disk, the electronic processing of the digitally encoded image includes (1) digitally processing the digitally encoded image to measure lengths and widths of the identification codes of the disks, and (2) electronically comparing the measured lengths and widths with premeasured and electronically stored identification code lengths and widths to automatically distinguish the identification code of the reference disk from among the identification codes of the other disks on the plate.

Where the unique reference characteristic is an ordered pair or ratio of the numbers of light and dark pixels in an identification code, the electronic processing of the digitally encoded image includes (1) digitally processing the digitally encoded image to derive outlines of the identification codes on the disks, (2) further processing the digitally encoded image to count light pixels and dark pixels within the derived outlines of the identification codes on the disks, (3) computing, for each of the disks, a ratio of the respective counted light pixels and dark pixels, and (4) electronically comparing the computed ratios with stored identification code light/dark ratios to automatically distinguish the identification code of the reference disk from among the identification codes of the other disks on the plate.

The present invention is also directed to an associated method comprising optically scanning a plurality of drug diffusion disks on an agar plate and the drug identification codes on the disks, generating a digitally encoded image including digitized representations of the identification codes, and digitally processing the digitally encoded image to determine, for at least one of the identification codes on the disks, a numerical value of at least one overall pattern parameter. The determined numerical value of the pattern parameter is electronically compared with electronically stored premeasured values of the pattern parameter for the identification codes on the disks, to automatically identify at least one disk from among the disks on the plate.

In accordance with another feature of the present invention, the pattern parameter taken from the group consisting of (a) a total identification code area, (b) an ordered pair of identification code length and width, and (c) an ordered pair of light and dark identification code areas.

Where the disks have a preselected relative arrangement on the plate and the one disk constitutes a reference disk, the method further comprises electronically storing a characterization or identification of the preselected arrangement of the disks, the characterization or identification including for each disk a respective antibiotic agent identification code and a location relative to other disks in the arrangement. The method also comprises automatically or electronically determining the identities of the antibiotic agents on the disks in accordance with the preselected arrangement and the reference disk.

In most cases of machine operation, numerical pattern parameter values are determined for each of a plurality of identification codes on the disks. At least some of the determined numerical values of the pattern parameter are electronically compared with electronically stored premeasured values of the pattern parameter associated with the different disks on the plate.

In accordance with another feature of the present invention, the method additionally comprises optically detecting microbe-growth inhibition zones arising about the diffusion disks after placement of the disks in contact with the nutrient medium, electronically determining diameters of the inhibition zones, and automatically computing drug concentration parameters for the antibiotic agents on the disks from the determined diameters of the inhibition zones.

The scanning of the disks is preferably undertaken by a digital camera after growth of a microbe on the microbe-growth medium on the plate.

In accordance with a further feature of the present invention, the electronic processing of the digitally encoded image includes executing an adaptive threshold method to locate the identification codes on the disks and further includes carrying out a 2-bin fast histogram classification of all disks to determine an optimal threshold for distinguishing between relatively light pixels and relatively dark pixels of the identification codes and background areas on the disks.

In accordance with an additional feature of the present invention, the electronic processing of the digitally encoded image further includes filtering the digitally encoded image to eliminate details and simplify the image. The filtering of the digitally encoded image may include digitally implementing a dilation and erosion operation.

In accordance with yet another feature of the present invention, the electronic processing of the digitally encoded image additionally includes determining an outline or code shape of the filtered image of each of the identification codes on the disks. Where the outlines or code shapes of the identification codes of the disks have respective lengths and widths, the electronic processing of the digitally encoded image also includes (i) digitally processing the outlines or code shapes of the identification codes of the disks to measure lengths and widths of the identification codes of the disks, and (ii) electronically comparing the measured lengths and widths with premeasured and electronically stored identification code lengths and widths to automatically distinguish the identification codes of the reference disk from among the identification codes of the other disks on the plate.

Pursuant to a further feature of the present invention, the electronic processing of the digitally encoded image also includes (a) applying an affine transformation to rotate identification code patterns (e.g., individual pixels or identification code outlines), and (b) comparing the rotated identification code patterns with pre-established code shapes. The comparing of the rotated identification code patterns with pre-established code shapes preferably includes computing a 2-dimensional correlation coefficient.

An associated apparatus in accordance with the present invention is for use in carrying out a microbiological assay utilizing a plurality of drug diffusion disks each carrying a respective antibiotic agent and each having an identification code identifying the respective antibiotic agent, wherein the disks are placed in contact with a nutrient medium on a plate and a microbial solution is deposited on the medium. The apparatus comprises an optical monitoring device for optically detecting microbe-growth inhibition zones arising about the diffusion disks after placement of the disks in contact with the nutrient medium and the deposition of the microbial solution on the medium and for optically scanning the identification codes on the disks to produce a digitally encoded image including digitized representations of the identification codes. The apparatus further comprises a processing system operatively connected to the optical monitoring device, the processing system being programmed to digitally process the digitally encoded image to determine, for at least one of the identification codes on the disks, a numerical value of at least one overall pattern parameter. The processing system is additionally programmed to electronically compare the determined numerical value of the pattern parameter with electronically stored premeasured values of the pattern parameter for the identification codes on the disks, to automatically identify at least one disk from among the disks on the plate.

In another aspect of the present invention, the processing system is programmed to digitally process the digitally encoded image to determine an angle of rotation of the plate relative to a pre-established reference frame (coordinate system), the processing system being additionally programmed to detect a region of the plate occupied by a unique subset of the disks.

In a further aspect of the present invention, the processing system is further programmed to identify the antibiotic agents on the disks in response to optically scanned information from the monitoring device, the processing system being also programmed to determine the respective diameters of the microbe-growth inhibition zones.

In an additional aspect of the present invention, the processing system includes generic integrated circuits modified by programming to determine at least one of (a) total identification code area, (b) an ordered pair of identification code length and width, and (c) an ordered pair of light and dark identification code areas.

In yet another aspect of the present invention, the disks have a preselected relative arrangement on the plate and the one disk constitutes a reference disk. The apparatus then further comprises a memory electronically storing a characterization or identification of the preselected arrangement of the disks, the characterization or identification including for each disk a respective antibiotic agent identification code and a location relative to other disks in the arrangement, the processing system including generic integrated circuits modified by programming to automatically or electronically determine the identities of the antibiotic agents on the disks in accordance with the preselected arrangement and the reference disk.

In accordance with another feature of the present invention, the processing system includes generic integrated circuits modified by programming to recognize microbe-growth inhibition zones arising about the diffusion disks after placement of the disks in contact with the nutrient medium, to electronically determine diameters of the inhibition zones, and, from the determined diameters of the inhibition zones, to automatically compute drug concentration parameters for the antibiotic agents on the disks.

In a microbiological testing apparatus and/or method in accordance with the instant invention, positions of antibiotic containing disks are automatically determined, without further operator intervention or opportunity for human error. The apparatus and method do not require orientation marks on the disks. Nor do the apparatus and method necessitate extensive computer processing as required by conventional OCR to read codes without an orientation mark. Thus, the microbiological testing apparatus and method of the invention are inexpensive to use.

DESCRIPTION OF THE PREFERRED EMBODIMENTS

Figure 1:
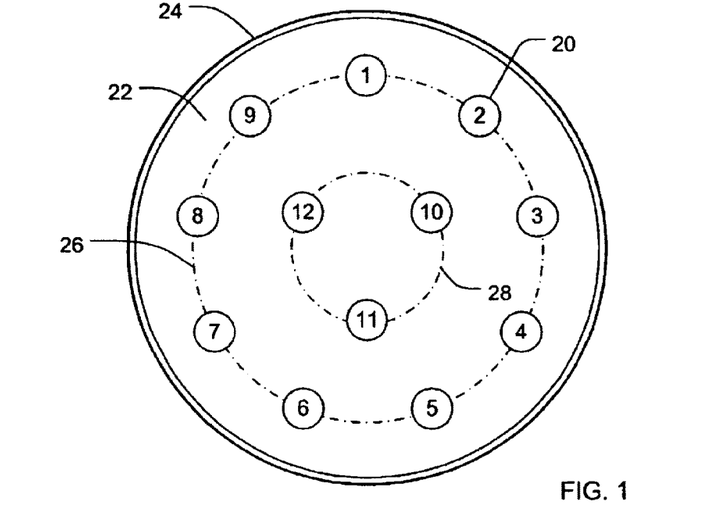
FIG. 1 is a schematic top plan view of an agar plate or disk dispenser panel, showing a common arrangement or configuration of antibiotic diffusion disks.
Figure 2:
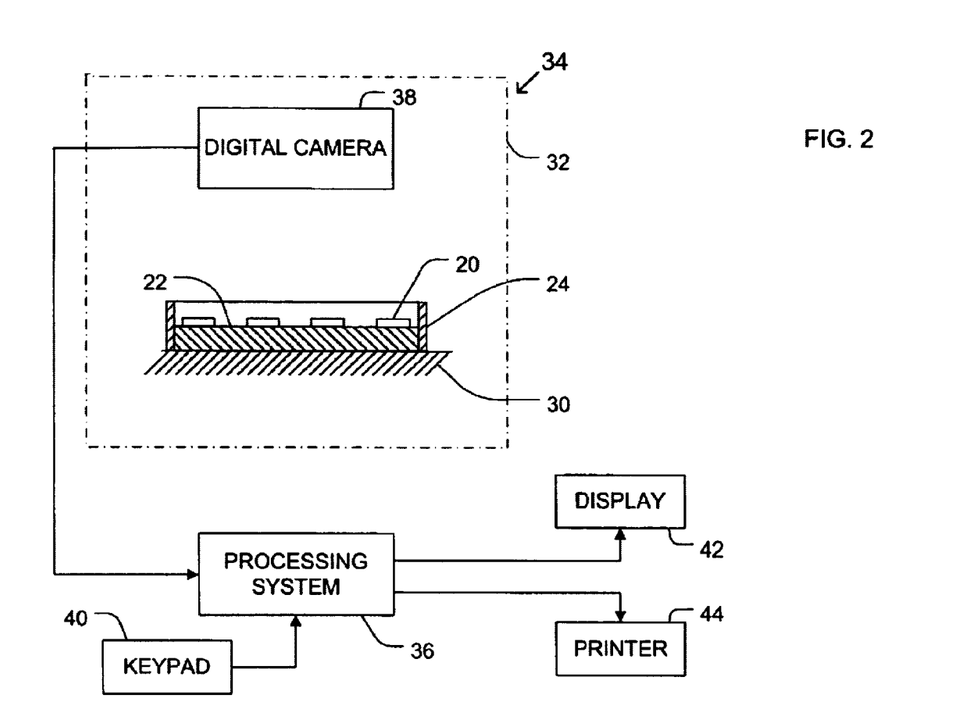
FIG. 2 is a schematic vertical cross-sectional view of the agar plate or disk dispenser panel of FIG. 1, showing the plate in a test plate reader machine, also showing a digital camera and a processing system.

With reference to FIGS. 1 and 2, drug diffusion disks 20 used in microbiological testing or assay procedures are placed by a disk dispenser (not shown) on a nutrient medium 22 on a plate or panel 24. Each disk 20 carries a respective antibiotic agent and bears an imprinted alphanumeric identification code identifying that antibiotic agent. Diffusion disks 20 are positioned on plate 24 in a preselected relative arrangement or pattern determined by the relative positions of disk-containing cylinders in the dispenser.

The identification codes on disks 20 are usually two to four characters on each of 1 or 2 lines. This code is usually completely visible on all disks 20 and not cut off by the disk edge. This code may be oriented in any direction on the disk due to the random placement on the plate 24 by the disk dispenser. Identification codes are currently printed in black ink on a white colored disk and provide sufficient contrast for analysis.

The majority of the users have disk dispensers for all sizes of plates. The most commonly used 150mm dispenser marketed by Bechton Dickinson deposits nine disks in an outer circle 26 (FIG. 1) and 3 disks in an inner circle 28. This geometry dictates that there are only three rotational independent orientations of the plate 24 if all twelve disks 20 are placed, that is, there are three possible orientations of plate 24 which result in the same disk pattern. If fewer than twelve disks are placed, one can derive similar constraints on plate orientation. For example, eleven disks 20 will have only one rotational independent orientation, ten disks may have one or two rotational independent orientations, nine disks may have up to nine rotational independent orientations (if all 9 disks are on outer circle 26), etc. For other dispenser sizes and shapes, similar considerations apply. As described in detail hereinafter, this information about constraints in possible plate orientations for a given disk pattern is combined with detection of unique disk identification code characteristics to greatly speed recognition of the orientation of a plate 24 in a drawer 30 of a test plate reader 32 (FIG. 2).

As depicted in FIG. 2, test plate reader 32 is part of a microbiological testing apparatus 34 including a digital processing system or computer 36. Testing apparatus 34 and particularly processing system 36 executes a plate orientation determination and an associated disk recognition process which are derived in part from a realization that antibiotic identification codes imprinted on diffusion disks 20 have readable shape features or analyzable parameters other than the alphanumeric characters themselves. Drug identification codes usually contain one to four alphanumerical codes printed on one line and zero to three numerical codes on a second line (zero code characters in the second line means no second line). These alphanumeric codes are thus associated with respective unique two-dimensional shapes on the disks 20. As discussed in detail hereinafter, particular features of the code shapes are extracted as quantifiable or numerical parameters. Generally, the code shapes are simplified during processing. The processed code shapes and/or the numerical parameters extracted from the code shapes are then electronically compared with code shapes or premeasured numerical parameters stored in memory. Sufficiently close correlation of a detected code shape or numerical parameter with a stored code shape or parametric value results in disk recognition. Disk recognition may be used to determine plate orientation or as a confirmation to proper disk placement.

Table 1 below sets forth the statistics as to the different available code combinations for one manufacturer (Becton Dickinson BBL™ Sensi-Disc™ for humans).

TABLE 1

| | | | | | | | | | | |
|---|---|---|---|---|---|---|---|---|---|---|
| # Characters on First Line | 1 | 1 | 1 | 2 | 2 | 2 | 3 | 3 | 3 | 3 |
| # Characters on Second Line | 1 | 2 | 3 | 1 | 2 | 3 | 0 | 1 | 2 | 3 |
| Total Count | 1 | 9 | 2 | 5 | 15 | 4 | 1 | 7 | 31 | 6 |

The notation mxn is used herein to denote a disk code having m alphanumerical characters on the first line and n numerical characters on the second line.

Where a particular disk pattern includes more than one rotational independent orientation, the present methodology preferably utilizes a numerically quantifiable shape feature in order to quickly identify at least one disk in the disk pattern, thereby determining which of the rotational independent orientations is present in the plate reader. Of the disks 20 on each drug plate or panel 24, shape-features on the disks are grouped. Of these groups, one group is selected based on containing few (1 or 2) disks as a target for initial identification to determine plate orientation in the reader drawer 30. For example, one identification code may have one line versus two lines for all other disks, or one identification code may have two characters on two lines, versus three characters on one or two lines for all other disks 20 on the plate 24. By focusing on fewer disks 20, recognition of the plate orientation is greatly speeded, thus eliminating the need to manually orient the reference disk (#1, FIG. 1) with the mark on the reader drawer 30.

Table 2 below sets forth statistics as to various code patterns for drug panels collected from four actual customer sites.

TABLE 2

| Number of Drug Panels | 1 × 1 | 1 × 2 | 1 × 3 | 2 × 1 | 2 × 2 | 2 × 3 | 3 × 0 | 3 × 1 | 3 × 2 | 3 × 3 |
|---|---|---|---|---|---|---|---|---|---|---|
| 1 | | 1 | | | 5 | | | | 5 | 1 |
| 1 | | | | | 3 | 1 | | 1 | 5 | 2 |
| 2 | | 1 | | 1 | 5 | | 1 | 1 | 2 | 1 |
| 2 | | | | 1 | 4 | | 1 | 1 | 1 | 1 |
| 3 | | | | | 5 | | 1 | 1 | 5 | |
| 3 | | | | | 5 | | 1 | 1 | 3 | 1 |
| 3 | | 2 | | 2 | 3 | | 1 | 1 | 1 | |
| 4 | | | | | 4 | | 1 | 1 | 5 | |
| 5 | | 3 | | 1 | 4 | | 1 | 1 | 1 | |
| 6 | | 3 | | 2 | 4 | | 1 | 1 | 1 | |
| 8 | | 2 | | 2 | 4 | | 1 | 1 | 1 | |

As mentioned above, one objective in performing an automated assay is to determine the orientation (angle about a vertical rotation axis) of plate 24 in the reader drawer 30. Inasmuch as the relative arrangement of disks 20 on plate 24 is predetermined by the disposition of disk-containing cylinders of magazines in a disk dispenser, the only unknown is the orientation of the disk in the reader drawer of the microbiological testing apparatus. Where the disk array has an asymmetrical configuration, for example, where a disk is missing from the outer circle 26 (FIG. 1), then the plate orientation can be determined by merely detecting the location of the missing disk. Where the disk array has two or more rotational independent orientations, the detection procedure necessitating the least data processing involves recognition of a single reference disk 20. This reference disk is preselected (since the entire collection of disks on a plate is known from the loading of the disk dispenser) for the reason that the reference disk bears an antibiotic identification code having a shape or at least one quantifiable shape feature or numerical shape parameter which is easily distinguishable from the shapes or quantifiable shape features of the other identification codes in the collection of disks on the particular plate 24. For example, if only one disk has exactly one line of alphanumeric characters, while all of the other disks in the particular plate arrangement have two lines of characters, then that one disk is selected to serve as the reference disk. As discussed in detail hereinafter, the reference disk may be identified as having the identification code with the least area, the greatest length to width ratio (or the least width to length ratio), the highest light to dark pixel ratio (or dark to light pixel ratio), the least number of outline points in a simplified or filtered electronic image, etc.

If we cannot distinguish between two plate orientations, for example, because a single reference disk is not present in the particular disk arrangement, a more extensive matching is applied. This higher level processing may entail, for instance, recognition of two disks. If the identification codes of two disks in an array have effectively the same shape (same quantifiable parameters, within machine error or tolerance) which is distinguishable from the shapes of the identification codes of the other disks in the array and if the two disks are placed at asymmetric locations in the array (e.g., not spaced by 180° in outer circle 26), then the identification of the two locations determines the plate orientation.

Thus, the present plate orientation determination method contemplates that, upon or during the loading of a disk dispenser, the identities of the disks in the various cylinders of the disk dispenser and the relative positions of the disks are recorded. A reference disk is first sought from among the set of disks, the reference disk having most unique identification code shape. Then, the spatial relationship of the other disks relative to that reference disk is determined. This spatial relationship forms an overall pattern/profile associated with each drug panel or plate generated from the same dispenser setup. The spatial disk relationship or arrangement is defined and saved during the drug-panel setup process. During drug panel setup, the system automatically records the above properties of each drug panel. If the system finds that it is not possible to determine the unique disk positions and plate orientation, the user will be warned, and the system will suggest an alternative disk layout to enable and facilitate such determination.

Another objective in performing an automated assay is to verify that the drug disks 20 are in the right positions on plate 24. After the disk positions and plate orientation are determined, all disks are checked to establish that they are in the right positions on test plate 24. First, a code shape matching method is performed. For antibiotic disks that are not unique in shape, a more complex pattern matching method is used as discussed below.

As further illustrated in FIG. 2, test plate reader 32 of testing apparatus 34 includes a digital camera 38 disposed above plate 24 for optically scanning the disks 20 on the plate and generating a digital signal encoding an image including digitized representations of the identification codes on the disks. This image signal is transmitted from digital camera 38 to processing system 36 where the image information is electronically processed to determine an angle of rotation of plate 24 relative to the reference frame or coordinate system of drawer 30. As demonstrated below, processing system 36 electronically analyzes the image information to detect a region of the plate 24 occupied by a unique subset of the disks 20 in the array on the plate.

Camera 38 has a field view of 150 mm at 800 pixels per line. With such a resolution capability, it is possible to obtain about thirty-two pixels for a disk 20 which is six millimeters in diameter. The identification code printed on a disk (e.g., made by Bechton Dickinson) is typically about 1 mm high, which translates to about five pixels per character and this is sufficient to distinguish between characters with a high degree of confidence.

As discussed above, testing apparatus 34 is recalibrated each time the associated disk dispenser is reloaded with a different selection of disks. This calibration may be undertaken by processing system 36 under instructions received from an operator via a keypad 40 (FIG. 2). In one alternative calibration procedure, the user merely identifies the disks (by antibiotic) and the relative locations of the disks on plate 24 (e.g., by sequential numbering as shown in FIG. 1). The shape profile information associated with the different identification codes is preloaded into processing system 36 at the factory. In another alternative calibration procedure, a sample set of disks 20 (for instance, the first disk array used upon loading of the disk dispenser) is scanned and the identification codes processed to determine the code shapes and the quantifiable or numerical shape parameters associated with each identification code. The processed code shapes and determined numerical code shape parameters are stored for subsequent use in electronic comparison operations. During the calibration process, processing system 36 also selects one or a few candidates to serve as a reference disk for initial code shape matching.

The microbiological testing apparatus 34 of FIG. 2 further includes output peripherals such as a display 42 and a printer 44 in part for enabling communication of testing results to an operator. The peripherals, particularly display 42, are also used during calibration procedures to guide and user and provide feedback.

Because the orientation or a plate 24 is not known initially, processing system 36 initially searches over a wide area, about 76 mm in diameter on a 150 mm plate, for a reference disk. All disks are then located on the plate 24 relative to the reference disk.

Figure 3:
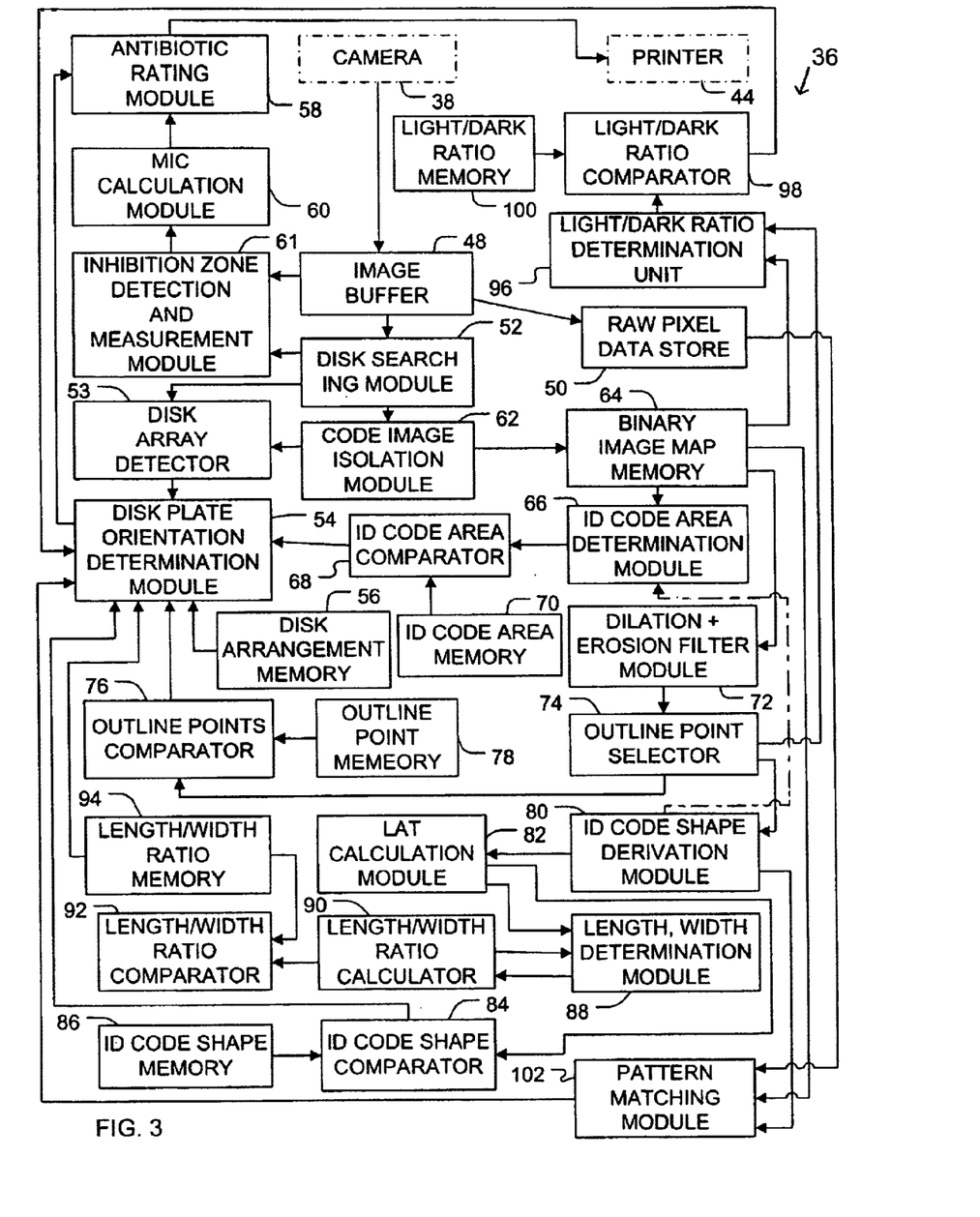
FIG. 3 is a block diagram of selected functional modules of the processing system of FIG. 2.
Figure 4:
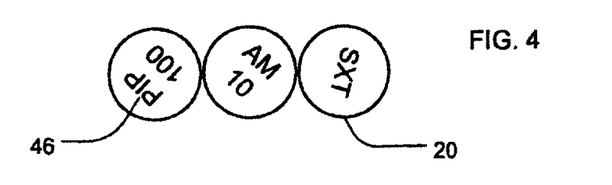
FIG. 4 is a grayscale image of three representative antibiotic diffusion disks, as encoded in a digital signal generated by the digital camera of FIG. 2.

As illustrated in FIG. 3, processing system 36 includes a buffer or interface unit 48 operatively connected at an input to camera 38. Camera 38 transmits, to buffer 48, a digital signal encoding a grayscale image of the disks 20 on plate 24, particularly including the identification codes on the disks. FIG. 4 shows a grayscale image of three representative antibiotic diffusion disks 20 including respective identification codes 46, as encoded in a digital signal generated by camera 38. The raw pixel bits or grayscale image data from camera 38 may be stored in a data store 50. This grayscale image data is also provided to a disk searching module 52 which analyzes the image data to detect the locations of identification codes 46 and the associated disks 20. Disk searching module 52 also functions to detect, in the disk pattern, disk locations which are devoid of a disk. As noted above, detection of a missing disk 20 may be sufficient to determine the orientation of plate 24 in reader drawer 30. To that end, disk searching module 52 is operatively connected to an array detector 53 which characterizes or defines the arrangement of disks 20 on plate 24. Array detector 53 is connected to a disk plate orientation determination module 54 which compares the detected disk arrangement, including the location of the missing disk, with the predetermined disk arrangement, array or pattern stored in a memory 56 during a calibration procedure as discussed above. This comparison results in a determination of the orientation of plate 24 in drawer 30, which is communicated to an antibiotic rating module 58 for association of the different antibiotics with MIC (minimum inhibitory concentration) measurements made by an MIC calculation module 60 in response to inhibition zone diameters determined by a detection and measurement module 61 operatively connected to disk searching module 52 and image buffer 48.

As further illustrated in FIG. 3, disk searching module 52 is operatively coupled at an output to a code image isolation module 62 which carries out an adaptive threshold process for locating the identification codes 46 on disks 20 and for extracting the code shapes. A one-time two-bin fast histogram classification is used by code image isolation module 62 to determine an optimal threshold for separating code pixels from background pixels. The histogram classification applies a recursive algorithm wherein average percentages of light and dark pixels are selected as an initial approximation (e.g., 25% dark and 75% light for code and background within each disk area). During the classification process, pixels are shifted from one bin to the other. When there is no further movement between bins, the code shape has been adequately isolated from the background.

Figure 5:
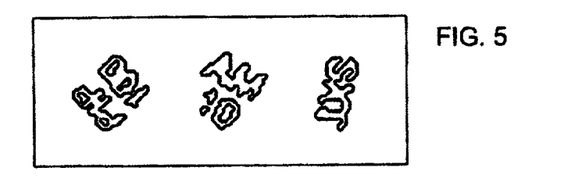
FIG. 5 is a binary or black and white image or representation resulting from a first level of processing of the diffusion disks of FIG. 4.

Code image isolation module 62 generates a binary image or representation as shown in FIG. 5. This image (or its reverse or negative) is stored in a memory 64 from whence the image is distributed to other modules of processing system 36 for further information extraction. For instance, memory 64 is connected to a module 66 which measures the areas subtended by the identification codes 46 of the different disks 20. Identification code area determination module 66 may function simply by counting the number of pixels of the respective identification codes (light pixels in the example of FIG. 5).

The identification code areas derived by module 66 are transferred to a comparator 68 which compares the derived identification code areas with the identification code area of a reference disk. The reference disk code area is stored in encoded form in a memory 70. Comparator 68 is linked to disk plate orientation determination module 54 for communicating thereto an identification (location) of the reference disk in the disk array on plate 24.

Figure 6:
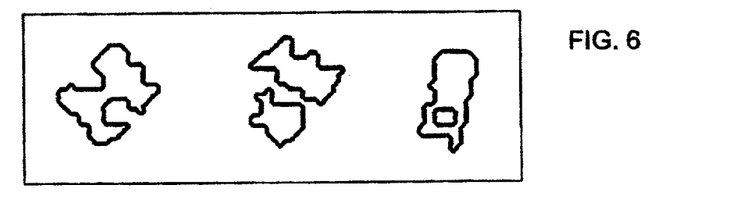
FIG. 6 is a binary or black and white representation resulting from a dilation-and-erosion-type filtering of the binary diffusion disk representation of FIG. 5.

As additionally illustrated in FIG. 3, binary image map memory 64 is also connected at an output to a filter module 72 which functions to smooth out or simplify the stored images of the identification codes by eliminating details of those images. More particularly, filter module 72 carries out a dilation and erosion operation, whereby each light pixel (identification code pixels) is expanded to cover one or two adjacent pixels in each direction and whereby the outer edges of the expanded light image are retracted or eroded by changing one or two light pixels all around the outer boundary of the identification code area to dark pixels. The dilation and erosion operation is executed according to a morphological operator $(X \oplus B_n) \ominus B_n$, where X is the binary code image, $B_n$ is a rounding operator of size n (preferably about the size of the character spacing in the identification codes, one or two pixels), $\oplus$ is the dilation operator and $\ominus$ is the erosion operator. A dilation operator followed by an erosion operator maintains the code shape while removing small inter-character variations. This simplification of image functions to speed matching calculations. FIG. 6 shows a binary disk code representation with a simplified or filtered shape produced by filtering module 72 from the binary diffusion disk representation of FIG. 5.

Figure 7:
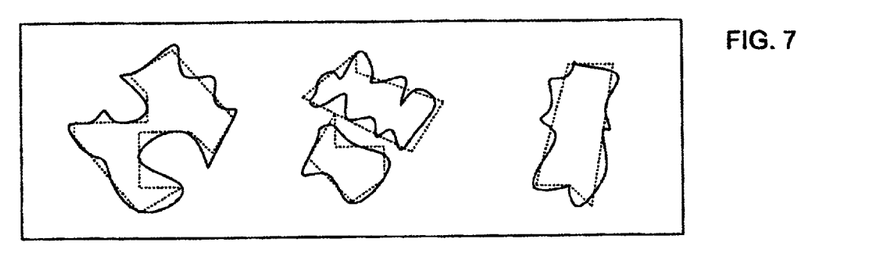
FIG. 7 is a binary or black and white representation similar to FIG. 6, showing derived identification code outlines laid over the simplified or filtered code shapes of FIG. 6.

The filtered identification code shapes are communicated by filtering module 72 to an outline point selector 74 which implements an even greater level of code shape simplification. In particular, outline point selector 74 analyzes each code shape from filtering module 72 to determine a number of corner points which may be connected, as illustrated in FIG. 7. Selector 74 may be connected to an input of a comparator 76 having another input connected to a memory 78 which stores outline point numbers associated with each identification code. Comparator 76 receives, from selector 74, an integer representing the number of outline or corner points of a processed identification code 46 and compares that integer with numbers stored in memory 78. Where the identification code 46 of a reference disk has a unique number of outline points, with respect to the disks 20 in the array on plate 24, the number of outline points can serve to identify the reference disk. An identification (location) of the reference disk thus detected is transmitted to disk plate orientation determination module 54.

It is to be noted that the simplified code shapes from filtering module 72 or the outlined code shapes from selector 74 may be optionally fed to area determination module 66. Thus, area computations and comparisons may be effectuated at a later juncture in the identification code processing sequence to yield additional possibilities of plate orientation determination and disk identification.

Figure 8:
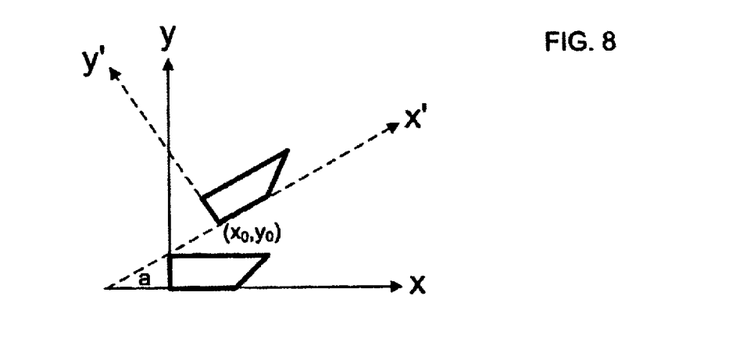
FIG. 8 is a graph illustrating a linear affine transformation in a comparison process carried out in accordance with the present invention.

The outline points determined by outline point selector 74 may be communicated to a module 80 which derives a simplified code shape for purposes of carrying out a code shape search. Such a search is implemented by an LAT (linear affine transformation) calculation module 82, a code shape comparator 84, and a memory 86 of pre-established simplified code shapes. LAT calculation module 82 computes, for each simplified code shape from module 80, a series of translated and rotated code shapes. LAT calculation module 82 operates using the following transformation:

$$\begin{bmatrix} x' \\ y' \end{bmatrix} = s \begin{bmatrix} \cos\alpha & \sin\alpha \\ -\sin\alpha & \cos\alpha \end{bmatrix} \begin{bmatrix} x - x_0 \\ y - y_0 \end{bmatrix}$$

where s is a dilation factor, $\alpha$ is a rotation angle and $x_0$, $y_0$ are translation coordinates (see FIG. 8). If the assumption is made that code prints by the same antibiotic disk manufacture have little variation in font size, dilation may be ignored. Also by using the geometric center of the code shape as the coordinates center, translation may be ignored.

LAT calculation module 82 may make the linear affine transformation computation in two ways. First, the transformation parameters problem is solved by using a few points (by linear regression) and calculating the mean square error of other points after the transformation. The second way is to apply the transformation on every small angle step and calculate the mean square error of all points.

LAT calculation module 82 may additionally be connected at an output to a module 88 for determining the lengths and widths of the processed code shapes. LAT calculation module 82 enables module 88 to select the proper orthogonal axes along which to measure the length and width of a processed identification code shape. Module 88 iteratively approaches a maximum difference between two orthogonal measurements or, alternatively, a maximum length to width ratio. In part to that end, module 88 is connected to a ratio calculation module 90.

It is to be noted in this regard that LAT calculation module 82 may be programmed to perform coordinate rotations in a series of predetermined angular steps. Thus, a first set of iterations may rotate a code shape 45° in each successive transformation calculation. Depending on the results of the calculations, intermediate angles may be selected for transformation.

Ratio calculation module 90 is connected to an input of a comparator 92 having another input receiving premeasured length-width ratios from a memory 94. Ratio comparator 92 is connected at an output to disk plate orientation determination module 54 so that, if necessary, the orientation of plate 24 in drawer 32 may be established on the basis of the numerical value of the length to width (or width to length) ratio.

Yet another numerical code shape parameter which may be used by processing system 36 for detecting the orientation of a disk plate or panel 24 in reader drawer 30 is the ratio of light pixels to dark pixels (or dark pixels to light pixels) within the boundaries of an identification code. To implement this basis of detection, outline point selector 80 is connected to a light/dark ratio determination unit 96 which is also coupled at an input to binary image map memory 64. Unit 96 functions to count the light and dark pixels within the outline derived or generator by selector 80 and forms a ratio between the two counts. A comparator 98 at an output of unit 96 seeks to match the light dark ratio with a predetermined ratio stored in a memory 100. The result of a positive match is delivered to disk plate orientation determination module 54.

It is to be noted that the simplified or processed code shapes or any of the numerical code shape parameters described above, as well as any other numerical index of code shape, may be used to simply locate one preselected reference disk (or two or a few reference disks) in the array of disks on the test plate 24. Alternatively, one or more of the quantifiable code shape features or numerical code shape parameters may be used to confirm the identities of all disks 20 on the plate 24.

For codes that are not unique in shape (e.g., 2×2 or 3×2 characters), a pattern matching is performed by a module 102 (FIG. 3) against pre-established code patterns or templates. The patterns and templates are in the form of either binary image or grayscale image. Thus, pattern matching module 102 is connected at inputs to raw pixel data store 52 and to binary image map memory 64. The matching method carried out by module 102 is based on correlation coefficients, which are normalized for mean variations between the disk images and templates.

Pattern matching module 102 includes an LAT (linear affine transformation) calculation component (not shown separately) which again defines pattern translation and rotation. If the code shape has certain geometric properties, only a limited number of angles need to be computed. Satisfactory conditions are met, for instance, where the code shape has, in whole or in part, the form of a square, rectangle or trapezoid. The correlation calculation may be done on either the binary image data obtained from binary image map memory 64 or the original gray scale image registered in raw pixel data store 50. Again, if possible, identification code shapes are pre-screened for quantifiable shape features, such as area and width/height aspect ratio, before having pattern matching module 102 perform the more extensive and expensive correlation calculation.

Because the translation affects the correlation coefficient of the two images, a small range of translational factors are considered by module 102 during the computation. Based on the thickness of the font used for code print on disk, ±3 pixels are generally sufficient for translation consideration (9 different sets of translational parameters). Note that this is only needed if the system cannot decide without considering translation.

The 2-D Correlation Coefficient is defined as $$r^2 = \frac{SS_{xy}^2}{SS_{xx}SS_{yy}},$$

where $$SS_{xy}=\Sigma xy'-\Sigma x\Sigma y,\ SS_{xx}=\Sigma xx'-(\Sigma x)^2,\ SS_{yy}=\Sigma yy'-(\Sigma y)^2,$$

x' is conjugate of x, $0 \leq r^2 \leq 1$. The larger the $r^2$, the better the correlation between the two images/templates. There are many ways to effectively calculate 2-D correlation coefficient, for example, using 2-D FFT and calculating correlation coefficient under Fourier domain significantly reduces computational complexity for large image sizes. It is not necessary to use it where, as here, images/templates are in relatively small sizes (20–25 pixels).

It is to be noted that pattern matching module 102 may function to match processed code shapes, for example, from code shape derivation module 80, either in addition to or in substitution for the matching of pixelated image information. Pattern matching module 102 is connected to disk plate orientation determination module 54 which may function in part as a comparator to determine whether the disks identified by pattern matching module 102 correspond to the identification codes or disk identities stored in memory 56. Disk plate orientation module 54 may be connected to display 42 (FIG. 2) or printer 44 for alerting an operator as to a disk discrepancy.

Although the invention has been described in terms of particular embodiments and applications, one of ordinary skill in the art, in light of this teaching, can generate additional embodiments and modifications without departing from the spirit of or exceeding the scope of the claimed invention. For example, it may be considered preferable to have module 66 determine areas of identification codes based on processed code shapes from shape derivation module 80. The key is to quickly measure a quantifiable feature or parameter of a reference disk identification code where the computed numerical value differs detectibly from the numerical values of the same quantifiable feature or parameter of the identification codes of the other disks 20 in an array on a plate 24. Accordingly, it is to be understood that the drawings and descriptions herein are offered by way of example to facilitate comprehension of the invention and should not be construed to limit the scope thereof.

What is claimed is:

1. A method for use in a microbiological assay procedure wherein a plurality of diffusion disks are placed on a nutrient medium on a plate, each of said disks carrying a respective antibiotic agent and each having an identification code identifying the respective antibiotic agent, said disks being positioned on said plate in a preselected relative arrangement, the method comprising:

optically scanning the disks on the plate;

in response to the optical scanning of said disks and the corresponding identification codes, generating a digitally encoded image including digitized representations of said identification codes; and     electronically processing said digitally encoded image to determine an angle of rotation of said plate relative to a pre-established reference frame or coordinate system, the electronic processing of said digitally encoded image including detecting a region of said plate occupied by a unique subset of said disks.

2. The method defined in claim 1 wherein the electronic processing of said digitally encoded image includes filtering the digitally encoded image to eliminate details and simplify the image.

3. The method defined in claim 2 wherein the electronic processing of said digitally encoded image additionally includes determining an outline or code shape of the filtered image of each of the identification codes on said disks.

4. The method defined in claim 3 wherein the outlines or code shapes of the identification codes of said disks have respective lengths and widths, the electronic processing of said digitally encoded image also including:

digitally processing the outlines or code shapes of the identification codes of said disks to measure lengths and widths of the identification codes of said disks; and     electronically comparing the measured lengths and widths with premeasured and electronically stored identification code lengths and widths to automatically distinguish the identification codes of said reference disk from among the identification codes of the other disks on said plate.

5. The method defined in claim 4 wherein the electronic processing of said digitally encoded image also includes (a) applying an affine transformation to rotate said outlines or code shapes, and (b) comparing the rotated outlines or code shapes with pre-established code shapes.

6. The method defined in claim 2 wherein the electronic processing of said digitally encoded image also includes (a) applying an affine transformation to rotate identification code patterns, and (b) comparing the rotated identification code patterns with pre-established code shapes.

7. The method defined in claim 6 wherein the comparing of the rotated identification code patterns with pre-established code shapes includes computing a 2-dimensional correlation coefficient.

8. The method defined in claim 2 wherein the filtering of the digitally encoded image includes digitally implementing a dilation and erosion operation.

9. The method defined in claim 1 wherein said unique subset of said disks includes a reference disk having a unique characteristic relative to other disks on said plate.

10. The method defined in claim 9 wherein the identification codes of said disks have respective areas, said unique characteristic being the area of the respective identification code on said reference disk, the electronic processing of said digitally encoded image including:

digitally processing said digitally encoded image to determine estimates of areas occupied by the identification codes on said disks; and     electronically comparing the determined area estimates with prestored identification code areas to automatically distinguish the identification code of said reference disk from among the identification codes of the other disks on said plate.

11. The method defined in claim 9 wherein the identification codes of said disks have respective lengths and widths, said unique characteristic being the length and width of the respective identification code on said reference disk, the electronic processing of said digitally encoded image including:

digitally processing said digitally encoded image to measure lengths and widths of the identification codes of said disks; and     electronically comparing the measured lengths and widths with premeasured and electronically stored identification code lengths and widths to automatically distinguish the identification code of said reference disk from among the identification codes of the other disks on said plate.

12. The method defined in claim 9 wherein the identification codes of said disks have respective ratios of light pixels to dark pixels, said unique characteristic being the light pixel to dark pixel ratio of the respective identification code on said reference disk, the electronic processing of said digitally encoded image including:

digitally processing said digitally encoded image to derive outlines of the identification codes on said disks;

further processing said digitally encoded image to count light pixels and dark pixels within the derived outlines of the identification codes on said disks;

computing, for each of the disks, a ratio of the respective counted light pixels and dark pixels; and     electronically comparing the computed ratios with stored identification code light/dark ratios to automatically distinguish the identification code of said reference disk from among the identification codes of the other disks on said plate.

13. The method defined in claim 1 wherein the electronic processing of said digitally encoded image further includes filtering the digitally encoded image to eliminate details and simplify the image.

14. The method defined in claim 13 wherein the filtering of the digitally encoded image includes digitally implementing a dilation and erosion operation.

15. The method defined in claim 1 wherein the electronic processing of said digitally encoded image additionally includes determining an outline or code shape of the filtered image of each of the identification codes on said disks.

16. The method defined in claim 15 wherein the outlines or code shapes of the identification codes of said disks have respective lengths and widths, the electronic processing of said digitally encoded image also including:

digitally processing the outlines or code shapes of the identification codes of said disks to measure lengths and widths of the identification codes of said disks; and     electronically comparing the measured lengths and widths with premeasured and electronically stored identification code lengths and widths to automatically distinguish the identification codes of said reference disk from among the identification codes of the other disks on said plate.

17. The method defined in claim 15 wherein the electronic processing of said digitally encoded image also includes (a) applying an affine transformation to rotate the outlines or code shapes, and (b) comparing the rotated outlines or code shapes with pre-established code shapes.

18. The method defined in claim 1 wherein the electronic processing of said digitally encoded image also includes (a) applying an affine transformation to rotate identification code patterns, and (b) comparing the rotated identification code patterns with pre-established code shapes.

19. The method defined in claim 18 wherein the comparing of the rotated identification code patterns with pre-established code shapes includes computing a 2-dimensional correlation coefficient.

20. The method defined in claim 1 wherein the electronic processing of said digitally encoded image includes:
   executing an adaptive threshold method to locate the identification codes on said disks; and
   carrying out a 2-bin fast histogram classification of all disks to determine an optimal threshold for distinguishing between relatively light pixels and relatively dark pixels of the identification codes and background areas on said disks.

21. The method defined in claim 1 wherein the detecting of said region includes detecting an absence of a disk in a location within said region.

22. The method defined in claim 1 wherein the detecting of said region includes detecting a pattern or configuration of disks in said region.

23. A method for use in a microbiological assay procedure wherein a plurality of diffusion disks are placed on a nutrient medium on a plate, each of said disks carrying a respective antibiotic agent and each having an identification code identifying the respective antibiotic agent, the method comprising:
   optically scanning the disks and the identification codes on said disks;
   in response to the optical scanning of said disks and the corresponding identification codes, generating a digitally encoded image including digitized representations of said identification codes;
   digitally processing said digitally encoded image to determine, for at least one of the identification codes on said disks, a numerical value of at least one overall pattern parameter; and
   electronically comparing the determined numerical value of said pattern parameter with electronically stored premeasured values of said pattern parameter for the identification codes on said disks, to automatically identify at least one disk from among the disks on said plate.

24. The method defined in claim 23 wherein said pattern parameter taken from the group consisting of (a) a total identification code area, (b) an ordered pair of identification code length and width, and (c) an ordered pair of light and dark identification code areas.

25. The method defined in claim 23 wherein said disks have a preselected relative arrangement on said plate and wherein said one disk constitutes a reference disk, further comprising electronically storing a characterization or identification of said preselected arrangement of said disks, said characterization or identification including for each disk a respective antibiotic agent identification code and a location relative to other disks in said arrangement, further comprising automatically or electronically determining the identities of the antibiotic agents on said disks in accordance with said preselected arrangement and said reference disk.

26. The method defined in claim 23 wherein the digital processing of said digitally encoded image includes determining, for each of the identification codes on said disks, a numerical value of at least one overall pattern parameter; and
   electronically comparing at least some of the determined numerical values of said pattern parameter with electronically stored premeasured values of said pattern parameter associated with the different disks on said plate.

27. The method defined in claim 23, further comprising:
   optically detecting microbe-growth inhibition zones arising about the diffusion disks after placement of the disks in contact with the nutrient medium;
   in response to the optical detection of said inhibition zones, electronically determining diameters of said inhibition zones;
   from the determined diameters of said inhibition zones, automatically computing drug concentration parameters for the antibiotic agents on said disks.

28. The method defined in claim 23 wherein the scanning of said disks includes operating a camera.

29. The method defined in claim 23 wherein the scanning of said disks is undertaken after growth of a microbe on said medium.

30. The method defined in claim 23 wherein the electronic processing of said digitally encoded image includes:
   executing an adaptive threshold method to locate the identification codes on said disks; and
   carrying out a 2-bin fast histogram classification of all disks to determine an optimal threshold for distinguishing between relatively light pixels and relatively dark pixels of the identification codes and background areas on said disks.

31. The method defined in claim 23 wherein the electronic processing of said digitally encoded image further includes filtering the digitally encoded image to eliminate details and simplify the image.

32. The method defined in claim 23 wherein the electronic processing of said digitally encoded image further includes filtering the digitally encoded image to eliminate details and simplify the image, the filtering of the digitally encoded image including digitally implementing a dilation and erosion operation.

33. The method defined in claim 23 wherein the electronic processing of said digitally encoded image additionally includes determining an outline or code shape of the filtered image of each of the identification codes on said disks.

34. The method defined in claim 23 wherein the electronic processing of said digitally encoded image also includes (a) applying an affine transformation to rotate identification code patterns, and (b) comparing the rotated identification code patterns with pre-established code shapes.

35. The method defined in claim 23 wherein the electronic processing of said digitally encoded image also includes (a) applying an affine transformation to rotate identification code patterns, and (b) comparing the rotated identification code patterns with pre-established code shapes, the comparing of the rotated identification code patterns with pre-established code shapes including computing a 2-dimensional correlation coefficient.

36. An apparatus for use in carrying out a microbiological assay utilizing a plurality of drug diffusion disks each carrying a respective antibiotic agent and each having an identification code identifying the respective antibiotic agent, wherein said disks are placed in contact with a nutrient medium on a plate and a microbial solution is deposited on said medium, said apparatus comprising:
   an optical monitoring device for optically detecting microbe-growth inhibition zones arising about the diffusion disks after placement of the disks in contact with the nutrient medium and the deposition of the microbial solution on the medium and for optically scanning the identification codes on said disks to produce a digitally encoded image including digitized representations of said identification codes; and a processing system operatively connected to said optical monitoring device, said processing system being programmed to digitally process said digitally encoded image to determine, for at least one of the identification codes on said disks, a numerical value of at least one overall pattern parameter, said processing system being additionally programmed to electronically compare the determined numerical value of said pattern parameter with electronically stored premeasured values of said pattern parameter for the identification codes on said disks, to automatically identify at least one disk from among the disks on said plate.

37. The apparatus defined in claim 36, wherein said processing system is further programmed to identify the antibiotic agents on said disks in response to optically scanned information from said monitoring device, said processing system being also programmed to determine the respective diameters of said microbe-growth inhibition zones.

38. The apparatus defined in claim 36 wherein said pattern parameter is taken from the group consisting of (a) total identification code area, (b) an ordered pair of identification code length and width, and (c) an ordered pair of light and dark identification code areas.

39. The apparatus defined in claim 36 wherein said disks have a preselected relative arrangement on said plate and wherein said one disk constitutes a reference disk, further comprising a memory electronically storing a characterization or identification of said preselected arrangement of said disks, said characterization or identification including for each disk a respective antibiotic agent identification code and a location relative to other disks in said arrangement, said processing system including generic integrated circuits modified by programming to automatically or electronically determine the identities of the antibiotic agents on said disks in accordance with said preselected arrangement and said reference disk.

40. The apparatus defined in claim 36 wherein said processing system includes generic integrated circuits modified by programming to:
    recognize microbe-growth inhibition zones arising about the diffusion disks after placement of the disks in contact with the nutrient medium;
    in response to the recognition of said inhibition zones, electronically determine diameters of said inhibition zones; and
    from the determined diameters of said inhibition zones, automatically compute drug concentration parameters for the antibiotic agents on said disks.

41. The apparatus defined in claim 36 wherein said optical monitoring device is a digital camera.

42. The apparatus defined in claim 36 wherein said processing system includes generic integrated circuits modified by programming to:
    execute an adaptive threshold apparatus to locate the identification codes on said disks; and
    carry out a 2-bin fast histogram classification of all disks to determine an optimal threshold for distinguishing between relatively light pixels and relatively dark pixels of the identification codes and background areas on said disks.

43. The apparatus defined in claim 36 wherein said processing system includes generic integrated circuits modified by programming to filter the digitally encoded image to eliminate details and simplify the image.

44. The apparatus defined in claim 36 wherein said processing system includes generic integrated circuits modified by programming to implement a dilation and erosion operation to thereby filter the digitally encoded image to eliminate details and simplify the image.

45. The apparatus defined in claim 36 wherein said processing system includes generic integrated circuits modified by programming to determine an outline or code shape of the filtered image of each of the identification codes on said disks.

46. The apparatus defined in claim 36 wherein said processing system includes generic integrated circuits modified by programming to (a) apply an affine transformation to rotate identification code patterns, and (b) compare the rotated identification code patterns with pre-established code shapes.

47. The apparatus defined in claim 36 wherein said processing system includes generic integrated circuits modified by programming to (a) apply an affine transformation to rotate identification code patterns, and (b) compute a 2-dimensional correlation coefficient for comparing the rotated identification code patterns with pre-established code shapes.

48. An apparatus for use in carrying out a microbiological assay utilizing a plurality of drug diffusion disks each carrying a respective antibiotic agent and each having an identification code identifying the respective antibiotic agent, wherein said disks are placed in contact with a nutrient medium on a plate and a microbial solution is deposited on said medium, said apparatus comprising:
    an optical monitoring device for optically detecting microbe-growth inhibition zones arising about the diffusion disks after placement of the disks in contact with the nutrient medium and the deposition of the microbial solution on the medium and for optically scanning the identification codes on said disks to produce a digitally encoded image including digitized representations of said identification codes; and
    a processing system operatively connected to said optical monitoring device, said processing system being programmed to digitally process said digitally encoded image to determine an angle of rotation of said plate relative to a pre-established reference frame or coordinate system, said processing system being additionally programmed to detect a region of said plate occupied by a unique subset of said disks.

49. The apparatus defined in claim 48 wherein said processing system includes generic integrated circuits modified by programming to:
    execute an adaptive threshold apparatus to locate the identification codes on the disks; and
    carry out a 2-bin fast histogram classification of all disks to determine an optimal threshold for distinguishing between relatively light pixels and relatively dark pixels of the identification codes and background areas on the disks.

50. The apparatus defined in claim 48 wherein said processing system includes generic integrated circuits modified by programming to filter the digitally encoded image to eliminate details and simplify the image.

51. The apparatus defined in claim 48 wherein said processing system includes generic integrated circuits modified by programming to determine an outline or code shape of the filtered image of each of the identification codes on the disks.

52. The apparatus defined in claim 48 wherein said processing system includes generic integrated circuits modified by programming to:
    determine an outline or code shape of the filtered image of each of the identification codes on the disks;

digitally process the outlines or code shapes of the identification codes of the disks to measure lengths and widths of the identification codes of the disks; and electronically compare the measured lengths and widths with premeasured and electronically stored identification code lengths and widths to automatically distinguish the identification codes of the reference disk from among the identification codes of the other disks on the plate.

53. The apparatus defined in claim 48 wherein said processing system includes generic integrated circuits modified by programming to (a) apply an affine transformation to rotate identification code patterns, and (b) compare the rotated identification code patterns with pre-established code shapes.

54. The apparatus defined in claim 48 wherein said processing system includes generic integrated circuits modified by programming to (a) apply an affine transformation to rotate identification code patterns, and (b) compute a 2-dimensional correlation coefficient for comparing the rotated identification code patterns with pre-established code shapes.

55. The apparatus defined in claim 48 wherein said processing system includes generic integrated circuits modified by programming to digitally implementing a dilation and erosion operation for filtering of the digitally encoded image.

56. The apparatus defined in claim 48 wherein the unique subset of the disks includes a reference disk having a unique characteristic relative to other disks on the plate, the identification codes of the disks having respective areas, the unique characteristic being the area of the respective identification code on the reference disk, said processing system including generic integrated circuits modified by programming to:

digitally process the digitally encoded image to determine estimates of areas occupied by the identification codes on the disks; and electronically compare the determined area estimates with prestored identification code areas to automatically distinguish the identification code of the reference disk from among the identification codes of the other disks on the plate.

57. The apparatus defined in claim 48 wherein the unique subset of the disks includes a reference disk having a unique characteristic relative to other disks on the plate, the identification codes of the disks having respective lengths and widths, the unique characteristic being the length and width of the respective identification code on the reference disk, said processing system including generic integrated circuits modified by programming to:

digitally process the digitally encoded image to measure lengths and widths of the identification codes of the disks; and electronically compare the measured lengths and widths with premeasured and electronically stored identification code lengths and widths to automatically distinguish the identification code of the reference disk from among the identification codes of the other disks on the plate.

58. The apparatus defined in claim 48 wherein the unique subset of the disks includes a reference disk having a unique characteristic relative to other disks on the plate, the identification codes of the disks having respective ratios of light pixels to dark pixels, the unique characteristic being the light pixel to dark pixel ratio of the respective identification code on the reference disk, said processing system includes generic integrated circuits modified by programming to:

digitally process the digitally encoded image to derive outlines of the identification codes on the disks;

further process the digitally encoded image to count light pixels and dark pixels within the derived outlines of the identification codes on the disks;

compute, for each of the disks, a ratio of the respective counted light pixels and dark pixels; and electronically compare the computed ratios with stored identification code light/dark ratios to automatically distinguish the identification code of the reference disk from among the identification codes of the other disks on the plate.

59. The apparatus defined in claim 48 wherein said processing system includes generic integrated circuits modified by programming to detect an absence of a disk in a location within the region.

60. The apparatus defined in claim 48 wherein said processing system includes generic integrated circuits modified by programming to detect a pattern or configuration of disks in the region.

* * * * *